(12) United States Patent
Laporte-Uribe

(10) Patent No.: US 11,857,347 B2
(45) Date of Patent: Jan. 2, 2024

(54) APPARATUS FOR MONITORING NUTRITION, ESPECIALLY FERMENTATION IN THE RUMEN OF A RUMINANT

(71) Applicant: José A. Laporte-Uribe, Herdecke (DE)

(72) Inventor: José A. Laporte-Uribe, Herdecke (DE)

( * ) Notice: Subject to any disclaimer, the term of this patent is extended or adjusted under 35 U.S.C. 154(b) by 0 days.

(21) Appl. No.: 17/787,704

(22) PCT Filed: Dec. 17, 2020

(86) PCT No.: PCT/EP2020/086850
§ 371 (c)(1),
(2) Date: Jun. 21, 2022

(87) PCT Pub. No.: WO2021/123038
PCT Pub. Date: Jun. 24, 2021

(65) Prior Publication Data
US 2023/0025459 A1   Jan. 26, 2023

(30) Foreign Application Priority Data

Dec. 19, 2019  (EP) .................................... 19217923

(51) Int. Cl.
*A01K 11/00*  (2006.01)
*A61B 5/00*  (2006.01)
(Continued)

(52) U.S. Cl.
CPC ............ *A61B 5/6861* (2013.01); *A01K 29/00* (2013.01); *A61B 5/01* (2013.01); *A61B 5/073* (2013.01);
(Continued)

(58) Field of Classification Search
CPC . A61B 2562/162; A61B 5/073; A61B 5/1455; A61B 5/4238; A61B 5/6861
See application file for complete search history.

(56) References Cited

U.S. PATENT DOCUMENTS 4,975,581 A * 12/1990 Robinson ............. A61B 5/6876
702/19

FOREIGN PATENT DOCUMENTS

WO     WO-02093145 A1 * 11/2002 ............ G01N 21/05
WO     WO2013003892 A1    1/2013
(Continued)

OTHER PUBLICATIONS

Robert O' Leary, "Attenuated Total Reflection Spectroscopy method for measuring dissolved CO2 concentration in Beer", VitalSensors Technologies, Jan. 1, 2005, USA (4 pages).
(Continued)

*Primary Examiner* — Michael J D'Abreu
(74) *Attorney, Agent, or Firm* — ICE MILLER LLP

(57) ABSTRACT

An apparatus for monitoring nutrition, especially fermentation in a rumen of a ruminant, is designed to be orally applied to the ruminant and to stay permanently in the rumen. The apparatus includes: a) at least one sensing unit for sensing a characteristic value of dissolved carbon dioxide in the liquor of rumen and/or reticulum; and b) at least one first communication unit for the wireless communication of data with a respective second communication unit outside the ruminant. The sensing unit includes at least one attenuated total reflectance (ATR) sensor.

16 Claims, 4 Drawing Sheets

(51) Int. Cl.
    *A01K 29/00*     (2006.01)
    *A61B 5/01*     (2006.01)
    *A61B 5/07*     (2006.01)
    *A61B 5/145*     (2006.01)
    *A61B 5/1459*     (2006.01)
    *A61B 5/1495*     (2006.01)

(52) U.S. Cl.
    CPC .......... *A61B 5/1459* (2013.01); *A61B 5/1495* (2013.01); *A61B 5/14507* (2013.01); *A61B 5/4238* (2013.01); *A61B 2503/40* (2013.01); *A61B 2560/0214* (2013.01)

(56) References Cited

FOREIGN PATENT DOCUMENTS

| | | | |
|---|---|---|---|
| WO | WO-2015121220 A1 * | 8/2015 | ............... A01K 1/12 |
| WO | WO2015121220 A1 | 8/2015 | |

OTHER PUBLICATIONS

Laporte-Uribe José A Ed-Pérez Jose Francisco et al., "The role of dissolved carbon dioxide in both the decline in rumen pH and nutritional diseases in ruminants", Animal Feed Science and Technology, Jul. 7, 2016, vol. 219, Amsterdam, NL (12 pages).
International Search Report for International Application No. PCT/EP2020/086850 dated Feb. 11, 2021 (4 pages).

* cited by examiner

APPARATUS FOR MONITORING NUTRITION, ESPECIALLY FERMENTATION IN THE RUMEN OF A RUMINANT

INTRODUCTION

This disclosure relates to an apparatus for monitoring nutrition, especially fermentation in the rumen of a ruminant like a cow, a goat, a sheep and the like.

Ruminants are in many countries of the world used to produce milk and/or to produce meat. Both the milk and the meat production per ruminant have increased significantly over the last decades. Responsible for this rise is on one hand the genetic improvement of the ruminants e.g. by breeding, and on the other hand a better understanding of the nutritional requirements of the cattle.

In particular, in larger herds of dairy cattle the feed management of the herd frequently needs optimization. In particular, acidosis shall be avoided. Ruminal acidosis is understood as an increase in acidity in the rumen and described as a decline of the pH of the rumen content for a period of time which is enough to have physiological consequents on the animal affected by it. In that regards, metabolic and respiratory acidosis is understood as the increase in acidity of the blood and other tissues. In ruminants metabolic and respiratory acidosis is strongly coupled to the decline in rumen pH. Therefore, attempts were made to measure the rumen pH value in situ.

Prior art describes a bolus with an included pH meter and a temperature sensor e.g. in GB 2 455 700 A. This pH sensor functions electrochemically, i.e. it uses a pH electrode for measuring the pH value. Such a system is disadvantageous, as the used sensor drifts already after some weeks of use in the rumen.

Nevertheless, research and documentations demonstrated that nutritional diseases in ruminants were in fact caused by the accumulation of rumen dissolved carbon dioxide and not to the concomitant decline in rumen pH (Laporte-Uribe, 2016, 2019).

Dissolved carbon dioxide is a molecule of carbon dioxide associated to a molecule of water (hydronium). In other words, dissolved carbon dioxide is the liquid form of carbon dioxide when in contact with water. Dissolved carbon dioxide is linked to the main rumen buffer system and its decline or increase during fermentation influence the final rumen pH.

Normally, rumen dissolved carbon dioxide accumulation is limited, because standard physicochemical properties of the rumen fluid promote the carbon dioxide removal via eructation. However, modern feeding diets are high in energy which affect viscosity of the rumen liquid. These diets also have small particle sizes (physically effective fiber) which reduce surface tension and reduce chewing and saliva secretion limiting buffer addition into the rumen digesta. The changes in physicochemical properties promoted by these diets, i.e. changes in viscosity and surface tension, might prevent the release of dissolved carbon dioxide from the rumen liquid. Due to the normal chemical equilibrium between carbon species, some of this dissolved carbon dioxide is transformed into bicarbonate, and thus, $CO_2$ is "holdup" or retained within the digesta. This same phenomenon will create an even larger postprandial dissolved carbon dioxide concentration in the rumen. For instance, fermentation after feeding leads to rumen pH decline and the holdup bicarbonate will be quickly transformed into dissolved carbon dioxide. Moreover, and due to the increase rumen liquor viscosity, the excess of dissolved carbon dioxide will be only slowly released, and it accumulates at high concentrations for extended periods of time. The increase in dissolved carbon dioxide affects rumen microorganisms and their product of fermentation the volatile fatty acids (the energy sources for ruminants). It also increases carbon dioxide absorption through the rumen wall, as dissolved carbon dioxide can diffuse almost freely into the body. The excess of carbon dioxide produces conditions of cellular hypercapnia and hypoxia that will lead to respiratory and metabolic acidosis and the onset of nutritional diseases in ruminants. Therefore, it is the rise in dissolved carbon dioxide and not the concomitant decline in rumen pH that trigger these diseases.

Therefore, monitoring the concentration of dissolved carbon dioxide in the rumen can be used to predict, prevent and control the onset of rumen acidosis, subacute rumen acidosis, metabolic and respiratory acidosis, bloat, abomasal dysplasia, low milk fat syndrome and other nutritional syndromes and diseases associated to carbon dioxide holdup and/or foam formation in the gastrointestinal tract of ruminants.

On the other hand, the rise of rumen dissolved carbon dioxide during normal conditions produces a physiological response in the rumen epithelia that stimulate nutrient uptake and enhances milk productivity. In simple terms, dissolved carbon dioxide provides a signal for nutrient availability and the body reacts by absorbing more energy; this effect leads to greater milk productivity (Laporte-Uribe, 2019). Thus, monitoring dissolved carbon dioxide in vivo is advantageous in both ways: a way to avoid the onset of nutritional diseases and a way to promote better and more efficient rumen fermentation (Laporte-Uribe, 2019).

WO 2015/121220 describes a method and an apparatus for monitoring nutrition, especially fermentation in the rumen of ruminants, wherein the concentration of dissolved carbon dioxide is measured. The apparatus comprises a sensor having a measurement chamber into which the dissolved carbon dioxide can diffuse, and the concentration of dissolved carbon dioxide can be indirectly estimated, e. g. through a polytetrafluorethylene (PTFE) membrane. However, this methodology rely on the constant flux of carbon dioxide thorough the membrane and dietary changes might modify rumen physiochemical properties which also affect gas influx through the PTFE membrane. Thus, the amount of dissolved carbon dioxide by this method might be underestimated.

SUMMARY

An object of the present disclosure, per an embodiment, is to provide an improved apparatus for monitoring nutrition, especially fermentation in the rumen of ruminants, which eliminate the need for gas migration, reducing the effect of changes in physicochemical properties and can directly monitor dissolved carbon dioxide concentrations. This disclosure also suggests a methodology to use the information provided by the sensor or array of sensors to optimize milk productivity or prevent nutritional diseases in an individual basis, feeding groups or the whole herd of ruminants.

According to an aspect of the disclosure, per an embodiment, an apparatus for monitoring nutrition, especially fermentation in a rumen of a ruminant, wherein the apparatus is designed to be orally applied to the ruminant and to stay permanently and in direct contact with the rumen liquid, is proposed, comprising at least the following units:

a) at least one sensing unit for sensing a characteristic value of dissolved carbon dioxide in the rumen liquid and/or reticulum; and b) at least one first communication unit for the wireless communication of data with a respective second communication unit outside the ruminant, wherein the sensing unit includes at least one attenuated total reflectance (ATR) sensor.

c) a hermetic casing that provides protection from the outside environment.

d) An interphase that provide insight on the health and nutrition of an individual ruminant or a group (herd) of ruminants.

In particular, an aspect of the present disclosure, per an embodiment, is an apparatus for monitoring nutrition, especially fermentation in a rumen or in a reticulum of a ruminant, wherein the apparatus is designed to be orally applied to the ruminant and/or reticulum and to stay permanently and in direct contact with the rumen and/or reticulum liquid, wherein the apparatus comprises at least the following units:

a) at least one sensing unit for sensing a characteristic value of dissolved carbon dioxide in the liquor of rumen and/or reticulum; and b) at least one first communication unit for the wireless communication of data with a respective second communication unit outside the ruminant, wherein the sensing unit includes at least one attenuated total reflectance (ATR) sensor, wherein the sensing unit further comprises a light source emitting light, wherein a light channel is provided that leads light generated by the light source into a prism of the attenuated total reflectance sensor, said prism having a higher refractive index than rumen liquid and/or reticulum liquid, wherein the prism of the sensor is capable of being in direct contact with the rumen liquid and/or reticulum liquid, and wherein the apparatus comprises a hermetic casing that provides protection from the outside environment.

Accordingly, an aspect of the present disclosure, per an embodiment, is a use of an apparatus for sensing a characteristic value of dissolved carbon dioxide in the liquor of rumen and/or reticulum, for monitoring nutrition, especially fermentation in a rumen of a ruminant, wherein the apparatus is designed to be orally applied to the ruminant and to stay permanently in the rumen and wherein the apparatus is like defined above.

The disclosure, per an embodiment, is based on attenuated total reflectance (ATR) spectroscopy especially on an infrared sensor using attenuated total reflectance as sampling technique.

The ATR sensor uses the phenomenon of total internal reflection. A beam of radiation passes through a prism and undergoes total internal reflection through the prism. A so-called evanescent wave is created. The evanescent wave protrudes only a few micros beyond the prism surface. The distance that the evanescent wave extends from the prism surface depends upon the material of the prism and the intensity of the light emitted. The prism of the sensor is in a direct contact with the rumen liquid and/or reticulum liquid. In contrast to the prior art sensors there is no need for carbon dioxide to migrate into a sampling chamber, thus giving a direct and more accurate determination of the dissolved carbon dioxide concentration in the rumen and/or reticulum liquid.

According to the disclosure, per an embodiment, the ATR sensor comprises of a prism. Prism in the meaning of the disclosure is not restricted to a special geometry. Prism in the meaning of the disclosure is an optical element which meets the requirements of an attenuated total reflectance. In other words, the prism in an embodiment has a higher refractive index than the sample. It is preferred, per an embodiment, a low-cost silicon ATR prism, cut as a trapezoid or rectangle (see figure). One side of the prism is in direct contact with the rumen fluid (sampling side). The total area of the prism exposed to the rumen liquid will be smaller than the size of the prism. This small surface on the sampling side can be achieved by using the cap of the bolus (cylinder) as a filter and cover of the channel, e.g. a rectangular opening on the stainless-steel cap, FIG. 1. The borders of the opening in the cap are angled to improve light scattering and reduce fouling. This configuration allows the light to generate large number of internal diffractions, whereas the small sampling area is designed to maximize light scattering and sample penetration. However, other configurations can be explored. The interior of the sensor's cap, that covers the prism, has an aluminum frame where the prism is inserted. It is sputtered with a refracting metal to achieve good refraction and avoid interference. Silicon sealing agent is spread in the cap to seal the borders of the sensor from environment. The prism is kept in place by pressure against the borders and the angle of the channel; the cap folds into the body of the stainless-steel casing by pressure. For this a male and female corrugated silicon stopper, a series of silicon O-ring and a silicon sealant agent are combined during assembling to hermetically close the junction.

The sensing unit comprises of a light source emitting infrared light. The preferable light source, per an embodiment, is a low powered infrared light emitting diode (IR-LED). These types of IR LED lights normally are used for $CO_2$ sensing (4228 nm) with a wavelength range from 3500 to 5000 nm and a spectral width of 500 nm, however few modifications are necessary for $dCO_2$ detection (4268 nm). As follows:

An essential part of the sensing unit designed, per an embodiment, is a light channel that leads the IR light generated by the IR-LED into the ATR prism. It also avoids that the photodiode detector, in the other side of the channel, capture the light emitted by the IR-LED before is diffracted into the ATR prism. The preferable material, per an embodiment, for the channel is high grade aluminum; however other material can be explored. The best configuration is an inverted U-shaped channel where the IR-LED light is placed in one of the tips of the U-shaped. The interior surface of the channel is sputtered with a highly refracting metal, e.g. aluminum or gold alloys, to ensure optimal light transmission into and out of the ATR prism. The shape of the channel is rectangular or circular. Most of the channel is covered by a thin sheet of aluminum, except for the base where the ATR prism is placed. Both ends of the channel are bent or curved to achieve: high diffraction of the scattered light, the optimal light incidence angle into the ATR prism and the optimal penetration of the IR-LED light into the sample. Those conditions provide greater advantages on signal repeatability and $dCO_2$ detection, according to certain embodiments. However, other shapes and configurations might be explored depending on the best setup for diffraction, refraction and penetration into the sample.

In the other end of the sensing unit's channel, the photodiode detector (PD) is placed. The PD collects the light scattered in the diffraction process by the prims. The intensity of the attenuated light signal detected by the PD is inversely proportional to the rumen $dCO_2$ concentration by the integration of the light within a narrow wavelength according to the Beer-Lambert law and equation.

One of the main issues of adapting this CO2 sensor to dCO2 measurement is a strong interferes with water (IR peak at 4700 nm). It is known in the literature that the CO2 sensors can be modified to achieve a narrower wavelength separation from, i.e. 600 nm to 100 nm, but this solution required greater power consumption, thus not suitable for wireless applications. A different solution is proposed that comprise to use another low powered IR-LED light and PD to target water at a different IR wavelength 1800-1950 nm and use this output to create a baseline for water content of the fluid. Thus, the dCO2 concentration can be subtracted from the differences between the water background and dCO2 signal. Alternatively, the water content of the rumen fluid is relatively constant (3 to 4% Dry Matter), and during calibration, the sensor output might be corrected by this effect. Nevertheless, the preferred process, per certain embodiments, will be defined according to the cost of development vs the accuracy of the measurement and the efficiency on the detection method.

An important feature of this sensor, per an embodiment, is the capacity of self-calibration, as rumen boluses are not retrievable. Because of the almost constant water content, the use water as a reference signal provides also the opportunity to use its background noise to account for the decline in performance overtime of the sensor (drift) and correct the dCO2 signal using standard algorithms. Measurements of water does not require continuous measurement, as the detection of dCO2 requires, only few recordings per day e.g. 24 times/day might be enough to optimize dCO2 estimations and the self-calibration process. Similarly, a daily average per feeding group or the herd average can be used to improve dCO2 detection, a process that can be done internally within the boluses (i.e. sending an average value from the receiver's CPU (control processing unit) back into the bolus for self-calibration) or externally after the data has been transferred and analyzed.

Another strategy to improved reliability and the strength of the scattered signal to optimize dCO2 determinations is to have a small diffraction surface area to increase the repeatability of the results. Algorithms have been also developed to improved dCO2 determinations using this effect. It was also proposed the use of a low power lock-in amplifier (LIA) to improve the signal to noise ratio by phase sensitive detection. In other words, identifying a specific reference frequency and phase within the variable input and amplifying that signal.

Another important feature, per an embodiment, of this bolus for optimizing dCO2 monitoring is the inclusion of a low power micro temperature sensor in contact with the stainless-steel casing to correct the dCO2 measurements by the ambient temperature (rumen or reticulum temperature). The temperature sensor also provides information about core body temperature of cattle. This information can be used to detect illness and monitor ruminants' health, improving nutritional disease detection.

The sensing unit also comprises of an energy harvester used to increase the battery lifetime by harvesting the small energy generated by rumen peristaltic movements and cattle motion. The raw signal from the accelerometer can be also used to monitor the health status (i.e. heat detection and lameness and other metrics) and provide further signals and alarms to the farmers.

All the sensors within the rumen bolus: dCO2, water, temperature and the accelerometer are controlled by a microcontroller unit (MCU). It controls also the storage and the wireless two-way communication with the receiver PCU placed in the ham and milking parlor. The microcontroller also monitors the battery life and charge.

It adjusts updates and controls different algorithms stored in the firmware. The MCU of the system also controls and monitors the two-way communication with the external receiver. For this the MCU includes a low power wireless transceiver and an antennae. The frequency of transmission depends on the defined network system, e.g. it could include sub GHZ 863/928 MHz or Lora 433/868/915 MHz. Both network systems provide good two-way communication in the rumen environment and transmission distances of 500 m radius. These distances provide coverage for most of barns and dairy sheds in the market. For most applications the signal transmission rate can be setup to Live date transmission every 15 min, 2 h or every milking (2-3 times per day).

In any case, the MCU also is equipped with a microSD-memory card. The total size of the memory is enough to organized, compress and store the information recorded every 15 sec until the receiver actively ask for the information to be transmitted from each unit. A positive signal of complete transmission from the receiver to the boluses might automatically erase the information stored; otherwise the information might remain in the bolus SD-card for another cycle, if the transmission was not completed. Another important aspect of the two-way communication between the rumen boluses and the external receiver, per an embodiment, is to maintain and update time synchronization and firmware update.

The network of rumen boluses can be integrated and coordinated by the receiver that acts as an RF unit providing two-way communication. A series of algorithms provide the PCU of the receiver with the capacity to synchronize and crosstalk with large number of units (up to 5000 units/herds). The receiver also connects directly with cloud base servers to update software and firmware, and upload information to monitor the equipment performance. A large virtual and physical memory allowed the PCU to calculate the sensor information and store the information of many devices for a period of 1 month. Daily reporting of the nutritional performance of the individual cattle, feeding groups and herd on farm can be created and displayed on the user interphase. The information is processed within the PCU of the receiver or through cloud-based services. The information will be used to benchmark the farm and for future veterinary diagnostics. Alert are generated for individual or groups or herds at risk of nutritional diseases. The information also is used to provide nutritional advice about the quantity and quality of the dietary treatments, improving the feed efficiency, i.e. increasing milk productivity by kilogram of feed.

A lithium-based battery provides the energy for the optimal performance of the rumen boluses. The final dimensions and characteristics depend on the maximum requirement to sustain the correct function of the sensors and components (LIA, MGU and RF units) for a period of at least 2 years, or for the production lifetime of the ruminant (~7 years). The main restrain on battery size and capacity is the size of the rumen bolus allocated to the ruminant.

The apparatus forms a so-called bolus and the monitoring takes place within the rumen, reticulum and/or the ventral sac liquor. A medical grade stainless steel casing and the specific gravity (>2.3 g/cm3) of the device from the rumen bolus within the rumen or reticulum liquid. Keeping the dCO2 sensor under the rumen fluid is important to reduce interference with gas CO2 present in the gas phase (cap), in the top of the dorsal sac of the rumen. The CO2 might interfere with the dCO2 determination if the rumen bolus is exposed to the gas cap (IR 4228 nm).

The dimensions of the bolus may also be important. It should be no longer than 150 mm and 30 cm diameter for large ruminant such as cattle and buffaloes and 100 mm and 18 mm diameter for small ruminants like sheep and goats. Silicon O-rings or other types of sealant agents will be used to hermetically seal the electrical components from the surrounded rumen liquid. This feature provides protection from the surrounding liquid. Rumen substance migration normally limited the operational life of rumen boluses i.e. rumen pH boluses. The pH sensor is open to the rumen environment and rumen substances can migrate into the electronics, reducing the life time of the sensors and destroying the electronics. Moreover, rumen pH devices can be harmful for ruminants, as heave metals and other substances use on these devices can leak back into the rumen fluid contaminating the rumen fluid. The hermetic casing proposed for our sensor solved these issues and improve operational lifetime.

It is preferred, per an embodiment, to monitor the concentration of dissolved carbon dioxide at discrete point of times, preferably in intervals of less than one minute. Nevertheless, it is possible to change this time interval, in particular based on pre-determined circumstances, e. g. for some time after feeding. This can be triggered by an outside signal, e. g. from a communication unit combined with the feeding equipment or the like.

Furthermore, the gathered data can be used to generate information regarding the efficiency of fermentation in the rumen and the risk of nutritional diseases, including syndromes and diseases such as subclinical acidosis, acute acidosis, bloat, abomasal dysplasia, ketosis and others. This analysis can either be performed in an analysis unit in the apparatus or outside, after transmission via a first communication unit inside the rumen and a second communication unit being situated outside the animal. By this it is possible to generate specific warning signals for the farmer if specific criteria, like e. g. high dCO2 concentrations for 3, 5 or 12 h day.

Other features which are considered as characteristic for the disclosure are set forth in the appended claims, noting that the features presented individually in the claims can be combined in any technologically meaningful way and give rise to additional embodiments of the disclosure.

We described the use of dissolved carbon dioxide (dCO2) in the rumen of cattle to monitor and prevent nutritional diseases. In brief, the dissolved carbon dioxide (dCO2) holdup, in the rumen liquor due to physicochemical changes and fast fermentation of nutrients might explain many of the nutritional diseases and syndromes that are endemic of dairy farming. As a matter of example:

Rumen Acidosis and The dissolved carbon dioxide (dCO2) accumulation due Subacute Rumen Acidosis to physicochemical changes in the rumen liquor will trigger (SARA): rumen acidosis by reducing bacterial activity, decline of feed intake and nutrient digestion, prolonged period of high dissolved carbon dioxide (dCO2) concentrations will modify the acid-base balance of the rumen epithelia and increase in CO2 diffusion into the blood-stream will results in the establishment of metabolic and respiratory acidosis in cattle.

Abomasal dysplasia: The outflow of dCO2 saturated rumen liquor into the abomasum (true stomach) will mean that large amount CO2 and CH4 can be released in the abomasum after acid digestion, which will displace the abomasum to abnormal anatomical locations in the abdominal cavity, condition that has to be surgically corrected.

Bloat: The formation of stable foam in the rumen is a consequence and manifestation of the dissolved carbon dioxide (dCO2) holdup due to pH physicochemical changes of the rumen liquor during fermentation. Foam formation and stabilization in the rumen will inhibit eructation and animals will become tympanic. The condition, if severe, will lead to death of cattle.

Ketosis: The dissolved carbon dioxide (dCO2) holdup in the rumen will generate satiety signals that will limit feed intake, the reduction in nutrients intake will trigger fat mobilization and ketone body production, condition known as ketosis.

Low fat syndrome: The decline in acetic acid in favour of propionic acid production in the rumen will trigger the decline in fat content of the milk. High dissolved carbon dioxide (dCO2) concentrations in the rumen, on one hand stimulate the growth of bacteria that produce large amount of propionic acid. On the other hand acetogenic bacteria will favour other metabolic pathways reducing acetic acid production.

The apparatus, particular a wireless nutrition device can monitor the concentration and evolution of dissolved carbon dioxide (dCO2) in the rumen. The knowledge of threshold associated to the presentations of these diseases will allow farmers, nutritionist and consultants to design diets that promote better rumen fermentation and reduce the prevalence of nutritional diseases on farm.

The disclosure will help nutritionist and farmers to directly monitor rumen fermentation and will give a first account on feed quality, feeding management and animal performance by optimizing rumen bacterial growth. Farmers will be able to feed diets that provide the right balance of nutrient and feeding ruminant at the right time during the day to optimize feed conversion efficiency and milk production.

Fermentation monitoring is achieved by measuring the changes and evolution dissolved carbon dioxide (dCO2) concentration in the rumen liquor. Bacteria growth and metabolism are affecting by the changes in rumen dCO2 concentrations (Laporte-Uribe, 2016). Therefore, post-prandial changes and evolution of dissolved carbon dioxide (dCO2) concentrations might follow bacterial growth and monitoring dissolved carbon dioxide (dCO2) concentrations with an indwelling rumen bolus can provide an accurate measurement of bacterial fermentation.

The real-time monitoring of bacterial fermentation provides an opportunity to influence, particularly to optimize bacterial growth, for instance by reducing the time between lag phase and exponential growth, or by identifying when stationary growth phase begins, and/or by avoiding that rumen fermentation reaches decline phase of growth. In other words, the synchronization of growth cycles will improve the utilization of nutrient and overall production of by-products. Ultimately, most of the by-products of rumen bacterial growth are used as a source of energy for milk production; similarly, most of the protein in milk of dairy cattle comes from the digestion of rumen bacterial cells. Therefore, optimal rumen bacteria growth will mean also optimal energy and protein availability for milk production.

The identification and automatic warnings of bacterial growth and metabolism in the rumen can be used by farmers, nutritionist and consultants to improve feeding management routines. For instance, the addition of feed (feeding) at specific times of the day when the lack of nutrients reduce fermentation and bacterial growth might lead to increase feed efficiency conversion and nutrient uptake. Moreover, adjusting feeding management practices e.g. feeding time, will improves nutrient output by synchronizing and enhancing bacterial growth. The synchronization of nutrient supply with bacterial growth in the rumen also has been shown to improve feed intake, feed conversion efficiency, and milk production in dairy cattle.

Another relevant application could be the use of warning signals due to changes in bacterial growth to activate automatic feeding equipment (feeder and push-ups robots) to deliver feed to a specific animal, feeding group or herd. This can be achieved by transmitting the information obtained from the rumen of animals or group of cows equipped with the system, in real-time, to a central processing system that will control and activate the equipment to deliver feed. For that, the system will be designed to transmit the information, while the animal is been milked or emitting the information to receivers conveniently allocated around the ham, i.e. in the feeding area.

On the other hand, by analyzing dissolved carbon dioxide (dCO2) data transmitted wirelessly from single individual animal, feeding group or herd, the best daily routine of feeding for that particular individual or set of animals can be established. These feeding routines can be adjusted, after few hours of data processing, if changes in diet or component occurs, such as the opening of new batches of silage or the addition of new feed components. With this information an optimal feed intake can be obtained and higher milk production with lower nutritional problems might be achieved.

Monitoring bacterial growth and fermentation using dissolved carbon dioxide (dCO2) sensors becomes more important if we think on monitoring feed quality and feed composition. The evaluation of feed digestibility for ruminants can be easily monitored using in vitro gas production system; they provide an idea of the amount of fermentative material present in the different components of a ruminant diet. These systems are based on measuring the release of gas from the incubation of nutrient in a sealed container which mimics the in vivo fermentation in the rumen; CO2 is the main gas collected using this methodology. Dairy cattle diets also are set according to the nutrient content of the different components (evaluated separately); however the quality and quantity of nutrients on those components are highly variable on farm. Therefore, the mixing and a particular diet (with several components) do not warrant the provision of appropriated amount of nutrients for an adequate fermentation and milk production. This whole problem of quantity and quality of the diet is worsening by cattle's habits of feed selection while feeding.

Indwelling dissolved carbon dioxide (dCO2) rumen bolus and real-time monitoring of dissolved carbon dioxide (dCO2) evolution can be used as live monitoring of the digestibility of ruminant diets in a similar way as the in vitro system. The analysis of individual, feeding group and herd information will provide direct insight on the fermentative quality of the feed given to those animals. Because the feed information comes from the true intake of cattle, the information will reflect better the true nutritional value of the ration provided to each individual cow and also the whole herd.

For instance, a decline in the rumen exponential growth phase might indicate that specific diets lack of some of the nutrient required for optimal bacterial growth or if the stationary phase is reached faster with another diet, it might suggest that that particular diet is rich in highly fermentative material but might lack of the right amount of fiber for an adequate rumen fermentation. This information can be directly correlated to the milk yield for a single animal or group of cows (i.e. feeding group) and a clear idea of the nutrition value of a specific diet for feeding cattle can be achieved.

In other words, the information collected from a large set of animals within the herd will help to evaluate the nutritional value of the feed given in that specific herd or feeding group. Algorithms can be created to generate realtime warnings of the decline on feed quality or the lack nutrients that might limit optimal rumen fermentation (i.e. fiber content of the diet) and milk production. Therefore, farmers, nutritionist and consultants will be able to quickly modified quantities and components to optimize rumen bacterial growth, increase milk production and reduce nutritional diseases. As above, the integration with automatic feeding systems will enable the optimization of diets in a day by day basis, enhancing milk production and reducing nutritional diseases on farm.

Changes and saturation of rumen liquor with dissolved carbon dioxide (dCO2) can limit or change bacterial growth, bacterial metabolism and by-products of biochemical reactions of bacteria. The real-time monitoring dissolved carbon dioxide (dCO2) concentrations will enable to identify when different thresholds are reached and different biochemical pathway might be activated, which might alter the endproducts of that reactions. In similar way high dissolved carbon dioxide (dCO2) concentrations might shift bacteria populations in the rumen to groups that are better adapted to those environmental conditions; those bacteria might produce different end-products which in turn might change the overall concentration of nutrient in the rumen.

As an example and depending on other environmental conditions (mainly temperature) the following threshold can be found in the rumen. Optimal bacterial growth required dissolved carbon dioxide (dCO2) concentrations between ~12 mM and ~20 mM, on those conditions the main product of fermentation is acetic acid, higher concentrations (greater than 20 mM) might enhance propionic acid concentrations (~60 mM is optimal for large production of propionic acid in batch systems) and the increase in lactic acid production (~120 mM) might be seen due to excessive dissolved carbon dioxide (dCO2) accumulation.

Monitoring of dissolved carbon dioxide (dCO2) concentration in the rumen liquor will help farmers, nutritionist and consultants, not only to identify risk health factors such as excessive accumulation of lactic acid and propionic acid, but also to optimise propionic acid (main energy source for cattle and for milk protein production) and acetic acid production (milk fat production) to provide optimal milk quality (optimal milk protein/fat ratio). With this tool farmers, nutritionist and consultants might be able to design diets that promote better rumen fermentation for optimal milk quality production and might reduce risk factors associated to nutritional diseases. Algorithms will be designed to monitor in real-time dissolved carbon dioxide (dCO2) concentration providing relationship between short chain fatty acid concentrations (propionic, acetic, butyric and lactic acid) and thresholds will be established to correlate these important nutritional factors with milk quality.

Methane (CH4) is a waste product of fermentation and one of the main greenhouse gases in the atmosphere, by monitoring the methane concentrations during fermentation a good indication of amount of methane been produced by a specific animals and/or diet might be obtained. The dissolved CH4 concentrations can be measured directly with a specific NIRS sensor for methane and the evolution of methane during the day will give a good indication of the amount of CH4 produce for a certain animal, group of animals and diets.

The combination of methane sensor information with milk yield data per individual animals, feeding groups or herds will provide nutritionist and farmers with the possibility to adapt diets and minimize methane emissions. By feeding diets that can achieved a reduction in methane production during fermentation farmers could obtain higher feed conversion efficiency (more milk been produced per kg of feed given), or the selection of animals that digest diets with higher conversion efficiency (producing more nutrients and less methane).

An indirect approach for measuring conversion efficiency and methane emissions is by instead measuring dissolved carbon dioxide (dCO2) concentrations. There is a direct relationship between CO2 and CH4 production in the rumen; Methanogens bacteria produce CH4 by reducing H2 and CO2, this process is optimal at lower dissolved carbon dioxide (dCO2) concentrations (<60 mM) whereas higher dissolved carbon dioxide (dCO2) concentrations will tend to reduce CH4 formation, as other metabolic pathways for energy production might be favour, and/or other bacteria populations better adapted to thrive in high CO2 conditions replace Methanogens. Therefore, cataloguing animals between high and low dissolved carbon dioxide (dCO2) producer might find that animals with higher dissolved carbon dioxide (dCO2) concentrations or daily evolution tend to produce less methane and convert feed more efficiently than low dissolved carbon dioxide (dCO2) emitters.

In a similar way, bacterial populations in the rumen are unique and very stable for each individual animal, herd or group of animals. Establishment and maintenance of a particular bacterial population depends on the diet that animals received, but also on the internal environmental conditions of the rumen, most remarkably dissolved carbon dioxide (dCO2) concentration. Hence, fermentation characteristic measured by monitoring dissolved carbon dioxide (dCO2) concentrations and evolution will indicate which animals are more efficient into maintaining a large biomass of bacteria that are capable to digest nutrients more efficiently (less waste in the form of CH4). The relationship between dissolved carbon dioxide (dCO2) evolution and milk production of the animal might be a direct method to estimate fermentative efficiency and an indirect method to determine high methane emitters.

Algorithms and equations will be created to show, in a clear and consistent way, differences between and within animals, groups and herds. Similarly, methane production can be monitored externally and values correlated to dissolved carbon dioxide (dCO2) concentration and evolution measured directly. By combining CH4 emissions (real or estimated), dissolved carbon dioxide (dCO2) evolution and individual milk information, we can have a close approximation on the feed conversion efficiency and methane emissions. The information can be used by breeders, nutritionist, farmers and consultants to select more efficient animals (higher conversion feed efficiency, less methane (CH4) emissions), similarly the information might be used to select the most efficient diets or nutrients to minimize energy losses and CH4 emissions in a group or herd basis (optimal feed conversion efficiency for milk production).

Although the disclosure is illustrated and described herein as embodied in an apparatus for monitoring nutrition, especially fermentation in a rumen of a ruminant, it is nevertheless not intended to be limited to the details shown, since various modifications and structural changes may be made therein without departing from the spirit of the disclosure and within the scope and range of equivalents of the claims.

BRIEF DESCRIPTION OF THE FIGURES

The subject matter of the disclosure, however, together with additional objects and advantages thereof will be best understood from the following description of specific embodiments when read in connection with the accompanying drawings.

DETAILED DESCRIPTION

Figure 1A:
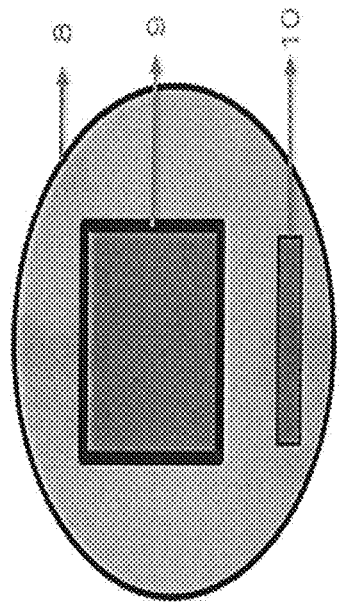
FIG. 1A-E shows an example of an apparatus
Figure 1B:
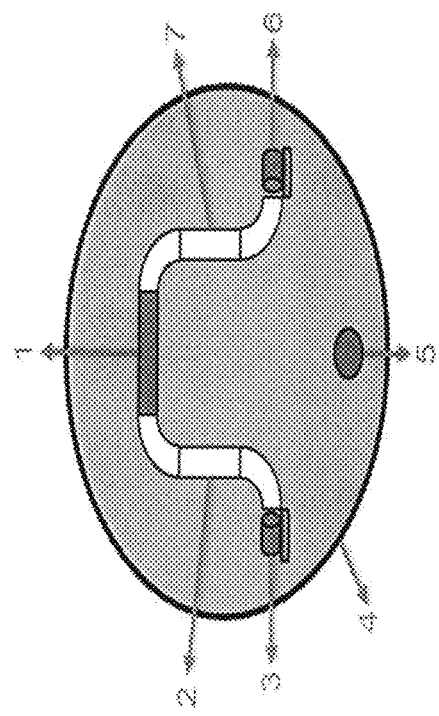
Figure 1C:
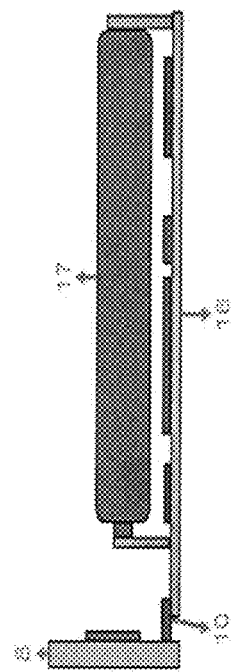
Figure 1D:
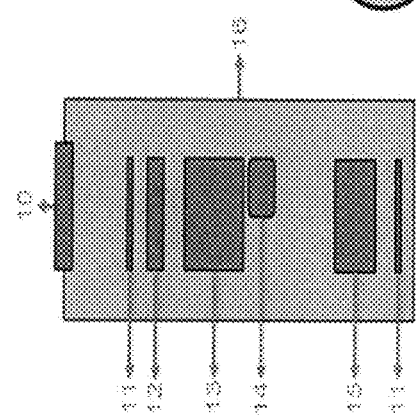
Figure 1E:
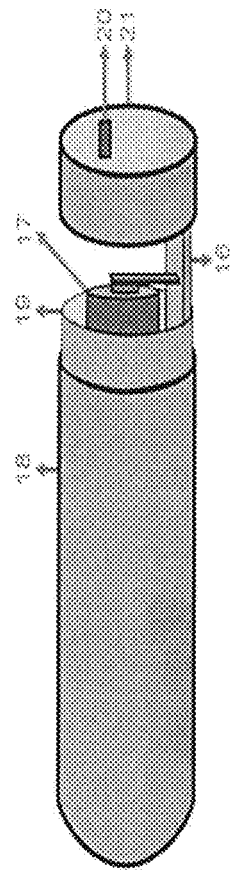

FIG. 1 shows an example of an apparatus 1 for monitoring nutrition, especially fermentation in a rumen of a ruminant, wherein a characteristic value of dissolved carbon dioxide inside the rumen is determined. The ATR sensor unit 8 includes several sensors. The IR-ATR dCO2 sensor itself 4 contains an IR-LED light for dCO2 and water 3 IR-LED light source. The light emitted by these sources is sent through the light channel 2 into the ATR prims 1 where the IR light is completely diffracted, a small amount of light in the evanescent wave penetrates the rumen fluid in contact with the small window 20 in the rumen bolus cap 21. The amount of light absorbed by the sample is directly dependent on the dCO2 and water concentrations. The remaining attenuated IR light travels throughout the channel 7 into the Photodiode detectors 6 where the attenuated signal for dCO2 and water is sensed. The sensor unit 8 also comprises of a temperature sensor 5 and an energy harvester accelerometer, 9. The sensor unit is connected with the mainboard 16 by an electrical connector, i.e. pin headers 10. The information from the IR-ATR sensor is sent into the low power lock-in amplifier or LIA 12 which amplified the IR signal improving dCO2 detection. The information is sent into the microcontroller unit, MCU 13. The temperature 5, accelerometer 9, water and the dCO2 signals are processed within the MCU 13, compile and send it into the SD card memory 14 for storage. The rumen bolus RF module 15 is in standby mode until the receiver 22 (see FIG. 2) provides the signal to transfer the information. The whole device is powered for a lithium based battery 17, kept in place by the holders 11. The stainless steel casing 18 provides a way to hermetically isolate the bolus from the rumen environment. The plug in cap 21 is kept in place by a corrugated and rubber sealed male connector 19.

Figure 2:
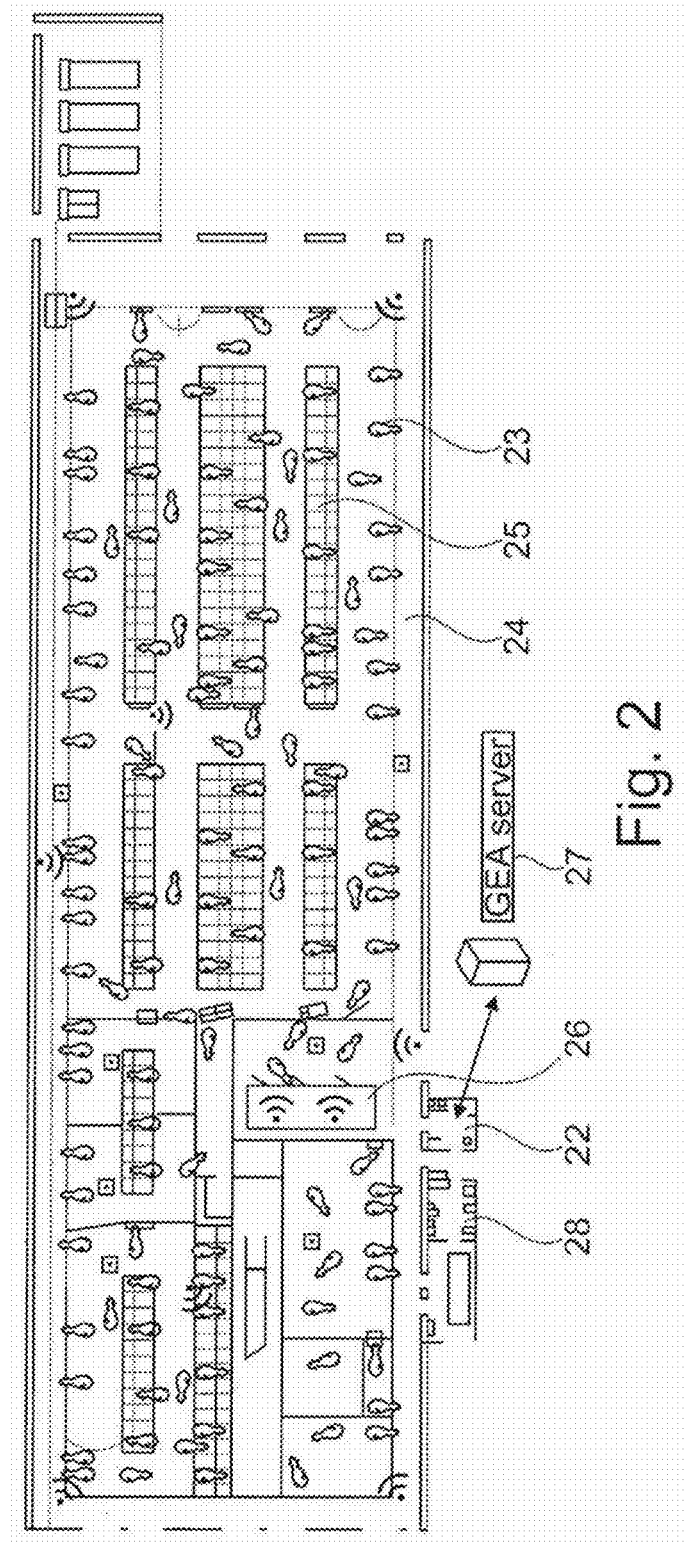
FIG. 2 shows the allocation of the equipment on the ham

FIG. 2 shows how the receiver 22 gathers the information from the ruminants in the barn. A network of antennas 26 allocated through the ham or diary shed to provided the network for the two-way communication between the receiver and the boluses RF module. The boluses transmit of the information and wait for positive confirmation from the receiver 22, once the receiver 22 confirm that the information has been appropriately received, the boluses returns to standby mode, the information stored in the SD-card 14 can be deleted.

The units 23, 24, 25 can be applied to individual animals e.g. in risk of ruminal acidosis, to sentinel animals, e.g. animals per feeding group or to the whole herd. The information stored in the boluses is transmitted at set intervals according to the protocols set in the receiver 22 by the user. The receiver also acts as interface; in here the information is further processed for optimization and to also include animals ID, date, feeding groups and other physiological and nutritional information per animal, herd and group. The receiver is in direct contact with the server 27 via internet and telephone services to provide firmware updates, equipment diagnostic and big data analysis. A user interface 28 might display the information analyzed in the receiver's PCU and information from cloud services. The analysis displayed in the user interface 28, information might include: health alarms, nutritional information for optimizing feed conversion efficiency and health status of cattle; see examples. The user interface 28 might also be used by the farmers to enter specific nutritional and physiological information, i.e. veterinary treatments, diet composition, etc., to improve the feedback and big data analysis.

Figure 3:
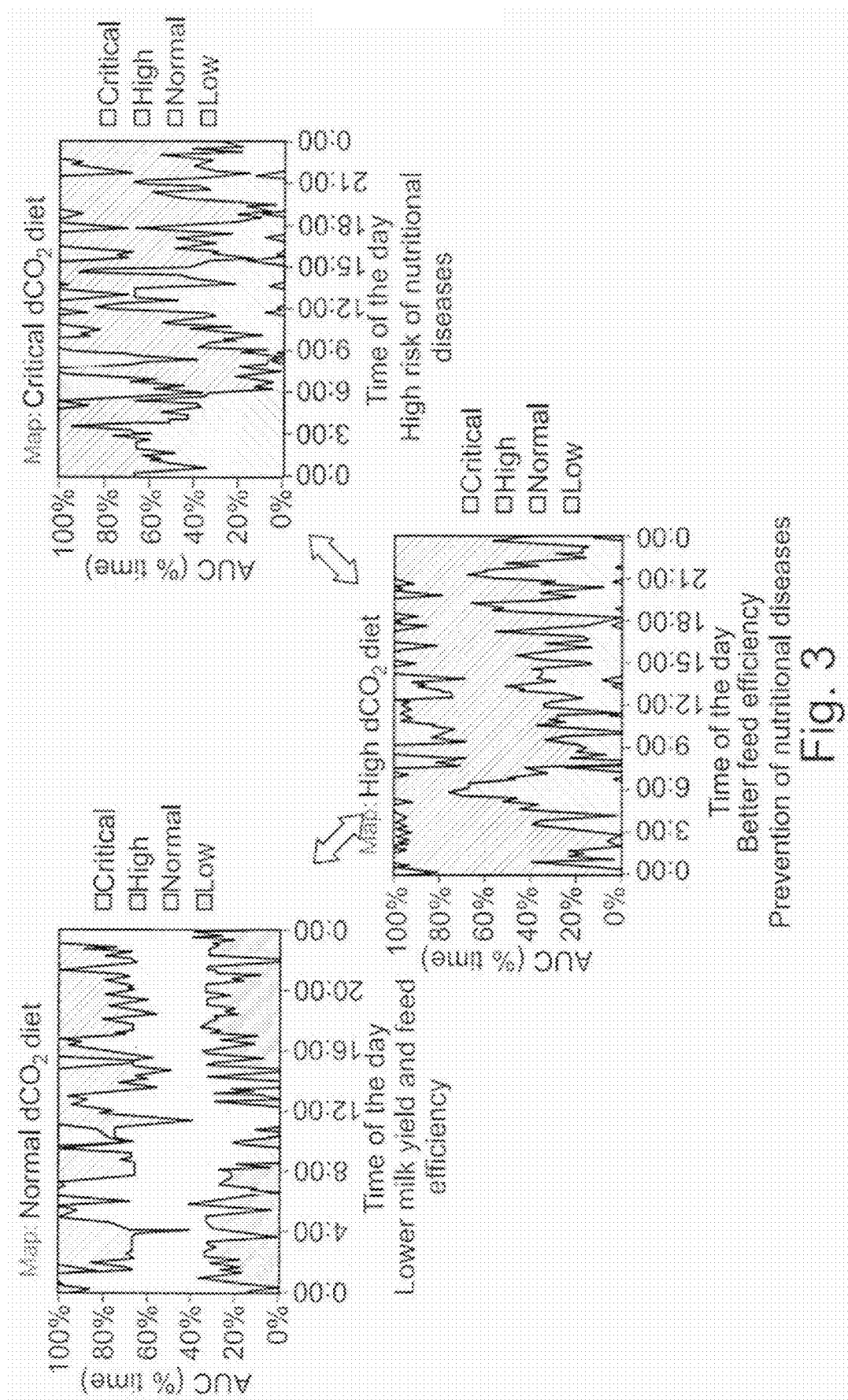
FIG. 3 shows a scheme of how the information is processed

FIG. 3 shows how the information gather from the rumen boluses can be used to monitor nutrition and cattle health. The advantages of the disclosure are, per an embodiment, that an optimal rumen $dCO_2$ concentrations lead to better anaerobiosis, higher milk productivity and lower risk of nutritional disease, high $dCO_2$ map or high $dCO_2$. High risk of nutritional disease can be found in diets that produce Critical $dCO_2$ MAP, whereas Normal $dCO_2$ MAP diets do not maximize feed conversion efficiency.

For instance, the boluses can be placed in the rumen of a sentinel cattle within feeding, all the animals in the herd, or risk cattle, prone to nutritional diseases. A receiver as a part of the second communication unit controls a two way communication with the at least one sensor, store data rom all sensing units and provide the data for a feeding management module.

A network of antennas that are conveniently deployed within a milking parlour, milking stall establish two-way communications, between apparatuses and the receiver. A feeding management module processes the information and provides analysis and recommendations.

To reduce power consumption the apparatus is preferably in a "hearing mode" stand by and is activated on request. In a case that continuous monitoring is preferred the apparatus records the information in predeterminate time intervals, preferably every 15 seconds, and the information is compiled, stored and sent in predeterminate time intervals, preferably every 10 minutes by the bolus. The receiver establishes communication protocols with the bolus and the receiver gives positive feedback to the boluses that information has been received. In the case that a communication is not stablished, the information is stored in a data storage 14. which is a part of the apparatus until the next uplink.

Preferably the apparatuses 1 are asked to send information by the receiver during milking session. Therefore, when cows enter the milking place and the receiver stablished communication with the apparatus, and the apparatus send information. The receiver gives positive feedback to the apparatus 1 that all information has been received. If a communication is not stablished, the information is stored until the next milking. The information achieved by the apparatus 1 is used for monitoring nutrition and to improve the animal health (see FIG. 3).

EXAMPLE

Rumen boluses are applied to the whole herd or sentinel animal within feeding groups. The information of the boluses is processed and rumen maps suggest that feeding management provide low $dCO_2$ concentrations (FIG. 4).

Diets are adapted by increasing starch, modifying the starch source and reducing the size of fiber on the total mix ration TMR. After further monitoring the sensors suggest that those modifications lead to the diet now provides high rumen $dCO_2$ concentrations FIG. 4.

Figure 4:
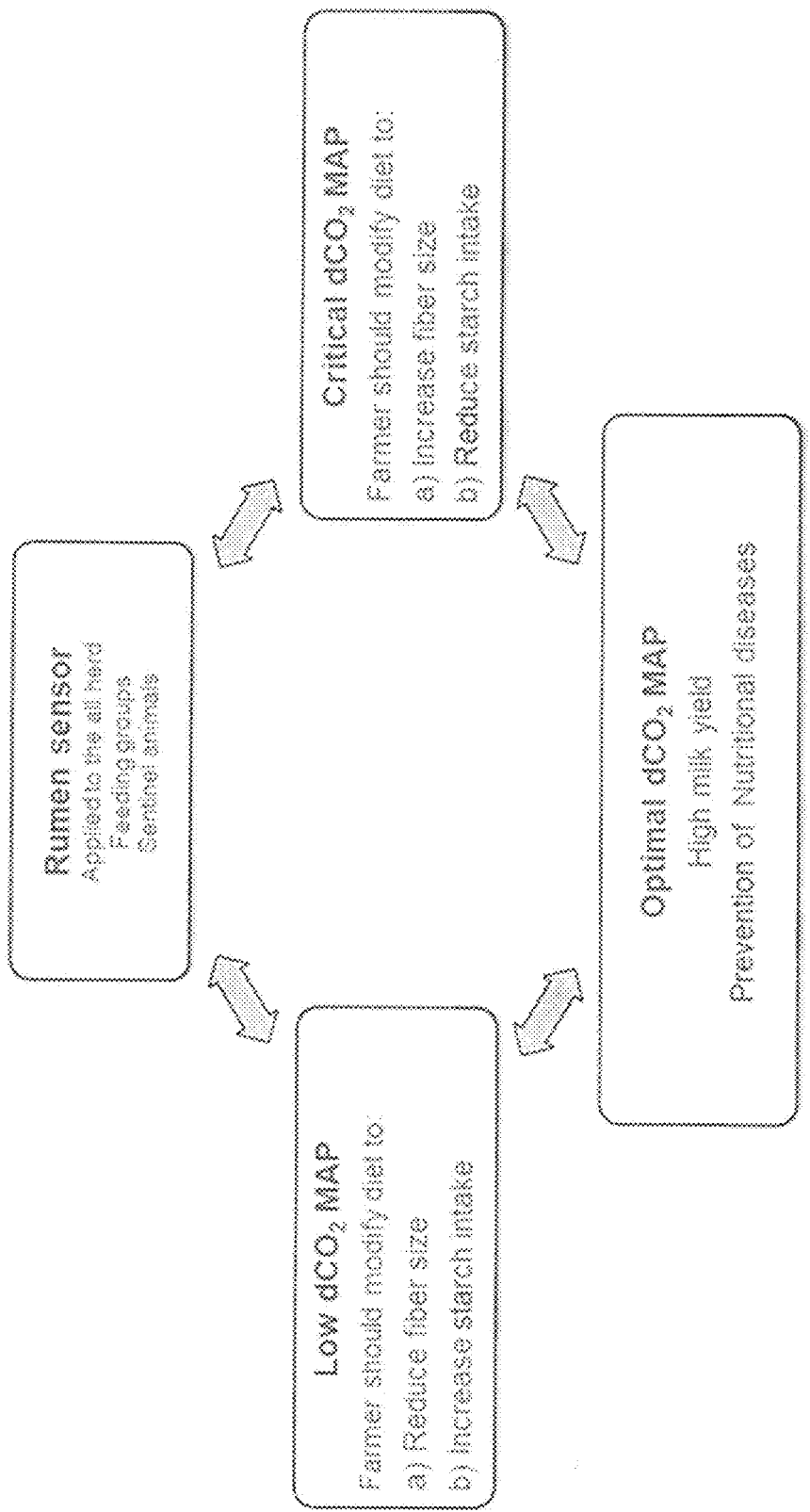
FIG. 4 describes how the results of that analysis are used to optimize feed intake and reduce the risk of ruminal acidosis.

The $dCO_2$ data might also suggest that the diet should be provided in 4 feeding bouts throughout the day to increase $dCO_2$ concentrations and avoid the rise of $dCO_2$ to critical values (see FIG. 4).

The data achieved by the boluses are also compared with the milk yield to find the optimal output for that particular diet.

All the recommendations are recorded and provided in a daily report.

The information can be also given to an automatic feeding system which uses the information to allocate feeding times and mixing conditions, preferably the type of components for example silage, hay and/or concentrates, and particle size to provide optimal $dCO_2$ concentrations.

All the features and advantages, including structural details, spatial arrangements and method steps, which follow from the claims, the description and the drawing can be fundamental to the invention both on their own and in different combinations. It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

LIST OF REFERENCE NUMERALS

1 ATR prims
2 light channel
3 IR-LED light source
4 ATR sensor
5 temperature sensor
6 photodiode detector
7 light channel (attenuated light)
8 Sensor unit
9 Energy harvesters, Accelerometer
10 Electronic connector
11 Battery holders
12 lock-in amplifier (LIA)
13 microcontroller (MGU)
14 micro-SD card
15 RF unit
16 mainboard
17 Lithium based battery 18 Stainless steel easing
19 Male connector for the plug-in cap
20 ATR prims window
21 Plug-in cap
22 Receiver
23 sensor in individual ruminants
24 sensors in sentinel group
25 sensors in groups
26 Antennas in the milking parlor and ham
27 server
28 Software interfaces

The invention claimed is:

1. Apparatus for monitoring nutrition and fermentation in a liquor in a rumen of a ruminant, wherein the apparatus is designed to be orally applied to the ruminant and to stay permanently and in direct contact with the rumen liquid in the rumen, the apparatus comprising at least the following units:
   a) at least one sensing unit for sensing a characteristic value of dissolved carbon dioxide in liquor of rumen, reticulum, or both the rumen and reticulum; and
   b) at least one first communication unit for wireless communication of data with a respective second communication unit outside of the ruminant,
wherein the at least one sensing unit includes at least one attenuated total reflectance (ATR) sensor to directly monitor the concentration and evolution of dissolved carbon dioxide and correspondingly to monitor carbon dioxide holdup in the liquor of the rumen without the need for gas migration.

2. Apparatus according to claim 1, wherein the at least one sensing unit comprises a light source emitting infrared light wherein the light source is an infrared light emitting diode.

3. Apparatus according to claim 2, wherein the light source emits an infrared radiation with a wavelength ranging between 4.25 and 4.30 um.

4. Apparatus according to claim 2, wherein the light source emits an infrared radiation with a wavelength of 4.27 μm.

5. Apparatus according to claim 1, wherein the apparatus is designed to remain permanently in direct contact with the rumen liquid, reticulum liquid, or both the rumen liquid and reticulum liquid and comprises
   c) a hermetic casing that provides protection from an outside environment.

6. Apparatus according to claim 1, wherein the ATR sensor comprises a prism with a higher refractive index than rumen liquid, reticulum liquid, or both rumen liquid and reticulum liquid and the prism of the ATR sensor is designed to be in direct contact with the rumen liquid, reticulum liquid, or both rumen liquid and reticulum liquid.

7. Apparatus according to claim 1, wherein the ATR sensor comprises a prism exposed directly to the liquid in the rumen or reticulum, wherein the prism is a silicone prism.

8. Apparatus according to claim 1, further comprising a temperature sensor for sensing the temperature in the rumen.

9. Apparatus according to claim 1, further comprising a casing made at least in part from stainless steel and with a specific gravity greater than 2.3 g/cm$^3$ to keep the apparatus on the rumen and the reticulum liquid.

10. Apparatus according to claim 1, wherein the at least one sensing unit has the capacity of self-calibration.

11. Apparatus according to claim 1, wherein the at least one sensing unit comprises a battery and an energy harvester used to increase battery lifetime by harvesting the energy generated by rumen peristaltic movements and cattle motion.

12. Apparatus according to claim 1, wherein the apparatus forms part of a network of rumen boluses.

13. Milking parlor, ham paddock or other type of ruminant housing structure and enclosure, comprising at least one second communication unit for wireless communication with a first communication unit in an apparatus according to claim 1.

14. Method for using an apparatus according to claim 1 for sensing a characteristic value a characteristic value of dissolved carbon dioxide in liquor of rumen, reticulum, or both the rumen and reticulum for monitoring nutrition, especially fermentation in a rumen of a ruminant, wherein the apparatus is designed to be orally applied to the ruminant and to stay permanently in the rumen.

15. Apparatus for monitoring nutrition and fermentation in a liquor in a rumen or in a reticulum of a ruminant, wherein the apparatus is designed to be orally applied to the ruminant, reticulum, or both the ruminant and reticulum and to stay permanently and in direct contact with the rumen liquid, reticulum liquid, or both the rumen and reticulum liquid, wherein the apparatus comprises at least:
   a) at least one sensing unit for sensing a characteristic value of dissolved carbon dioxide in the liquor of rumen, reticulum, or both rumen and reticulum; and
   b) at least one first communication unit for wireless communication of data with a respective second communication unit outside the ruminant,
   wherein the at least one sensing unit includes at least one attenuated total reflectance (ATR) sensor to directly monitor the concentration and evolution of dissolved carbon dioxide and correspondingly to monitor carbon dioxide holdup in the liquor of the rumen,
   wherein the at least one sensing unit further comprises a light source emitting light, wherein a light channel is provided that leads light generated by the light source into a prism of the at least one attenuated total reflectance sensor, said prism having a higher refractive index than rumen liquid, reticulum liquid, or both rumen and reticulum liquid, wherein the prism of the at least one attenuated total reflectance sensor is capable of being in direct contact with the rumen liquid, reticulum liquid, or both rumen and reticulum liquid, and
   wherein the apparatus comprises a hermetic casing that provides protection from an outside environment, wherein the hermetic casing is made at least in part from stainless steel with a specific gravity greater than 2.3 g/cm$^3$ to keep the apparatus on the rumen and the reticulum liquid, wherein the at least one sensing unit further has the capacity of self-calibration and comprises a battery and an energy harvester used to increase battery lifetime by harvesting the small energy generated by rumen peristaltic movements and cattle motion.

16. Apparatus according to claim 15, wherein the light source is an IR light source.

* * * * *